(12) United States Patent
Huter et al.

(10) Patent No.: US 6,575,995 B1
(45) Date of Patent: Jun. 10, 2003

(54) EXPANDABLE CAGE EMBOLIC MATERIAL FILTER SYSTEM AND METHOD

(75) Inventors: Benjamin Curtis Huter, Murrieta, CA (US); Andy Edward Denison, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 363 days.

(21) Appl. No.: 09/616,190

(22) Filed: Jul. 14, 2000

(51) Int. Cl.[7] ............................................. A61M 29/00
(52) U.S. Cl. ..................................................... 606/200
(58) Field of Search ................................. 606/200, 159

(56) References Cited

U.S. PATENT DOCUMENTS

| | | |
|---|---|---|
| 4,723,549 A | 2/1988 | Wholey et al. |
| 4,997,435 A | 3/1991 | Demeter |
| 5,100,425 A | 3/1992 | Fischell et al. |
| 5,158,548 A | 10/1992 | Lau et al. |
| 5,437,632 A | 8/1995 | Engleson |
| 5,769,816 A * | 6/1998 | Barbut et al. ............ 604/93.01 |
| 5,814,064 A | 9/1998 | Daniel et al. |
| 5,827,324 A | 10/1998 | Cassell et al. |
| 5,846,251 A | 12/1998 | Hart |
| 5,911,734 A | 6/1999 | Tsugita et al. |
| 5,980,555 A | 11/1999 | Barbut et al. |
| 5,989,281 A | 11/1999 | Barbut et al. |
| 6,066,158 A * | 5/2000 | Engelson et al. ........... 606/159 |
| 6,136,015 A * | 10/2000 | Kurz et al. ................. 606/191 |
| 6,203,561 B1 * | 3/2001 | Ramee et al. ............... 606/194 |
| 6,371,970 B1 * | 4/2002 | Khosravi et al. ........... 606/194 |

* cited by examiner

*Primary Examiner*—Michael J. Milano
*Assistant Examiner*—Gwen Phanijphand
(74) *Attorney, Agent, or Firm*—Fulwider Patton Lee & Utecht, LLP

(57) ABSTRACT

A system used in a blood vessel when an interventional procedure is being performed in a stenosed or occluded region, which is capable of enabling an expandable cage assembly therein, adapted to filter the blood in a blood vessel, to be expandable, so as to capture any embolic material that may be created and released into the bloodstream during the interventional procedure. The system includes a catheter which is positionable in a blood vessel at the interventional procedure site. The system further includes an expandable cage assembly, which is expandable and which may be deployed in the blood vessel distal to the interventional procedure site, which includes a plurality of struts, adapted to be expandable from unexpanded condition thereof, wherein each of the plurality of struts includes an element for varying the stiffness along the length thereof, for enabling the expandable cage assembly to be expandable, portions thereof which are in contact in the unexpanded condition, wherein the expandable cage assembly is capable of expanding, while preventing the unexpanded in contact portions thereof from sticking together during expansion and deployment thereof.

21 Claims, 3 Drawing Sheets

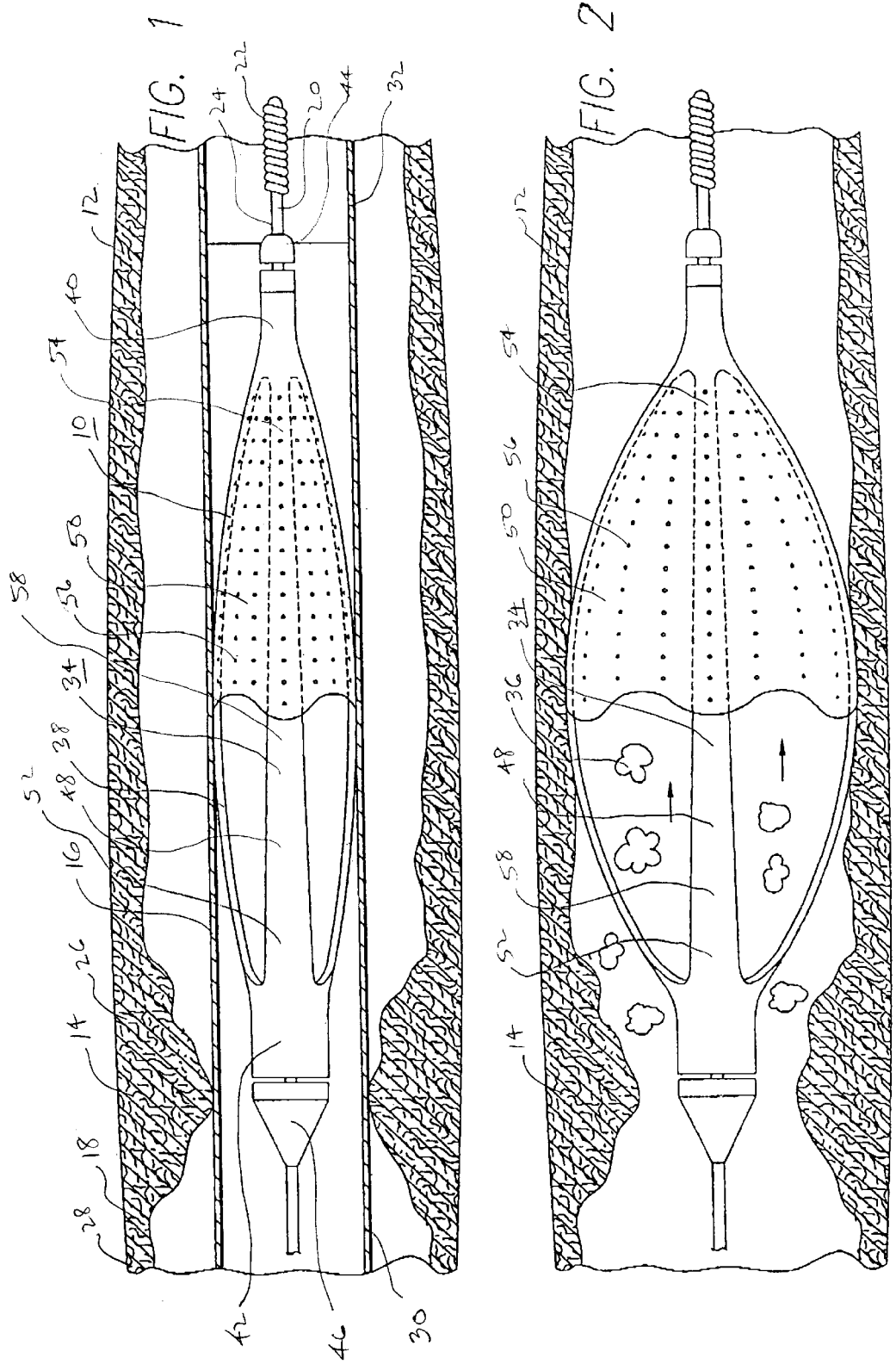

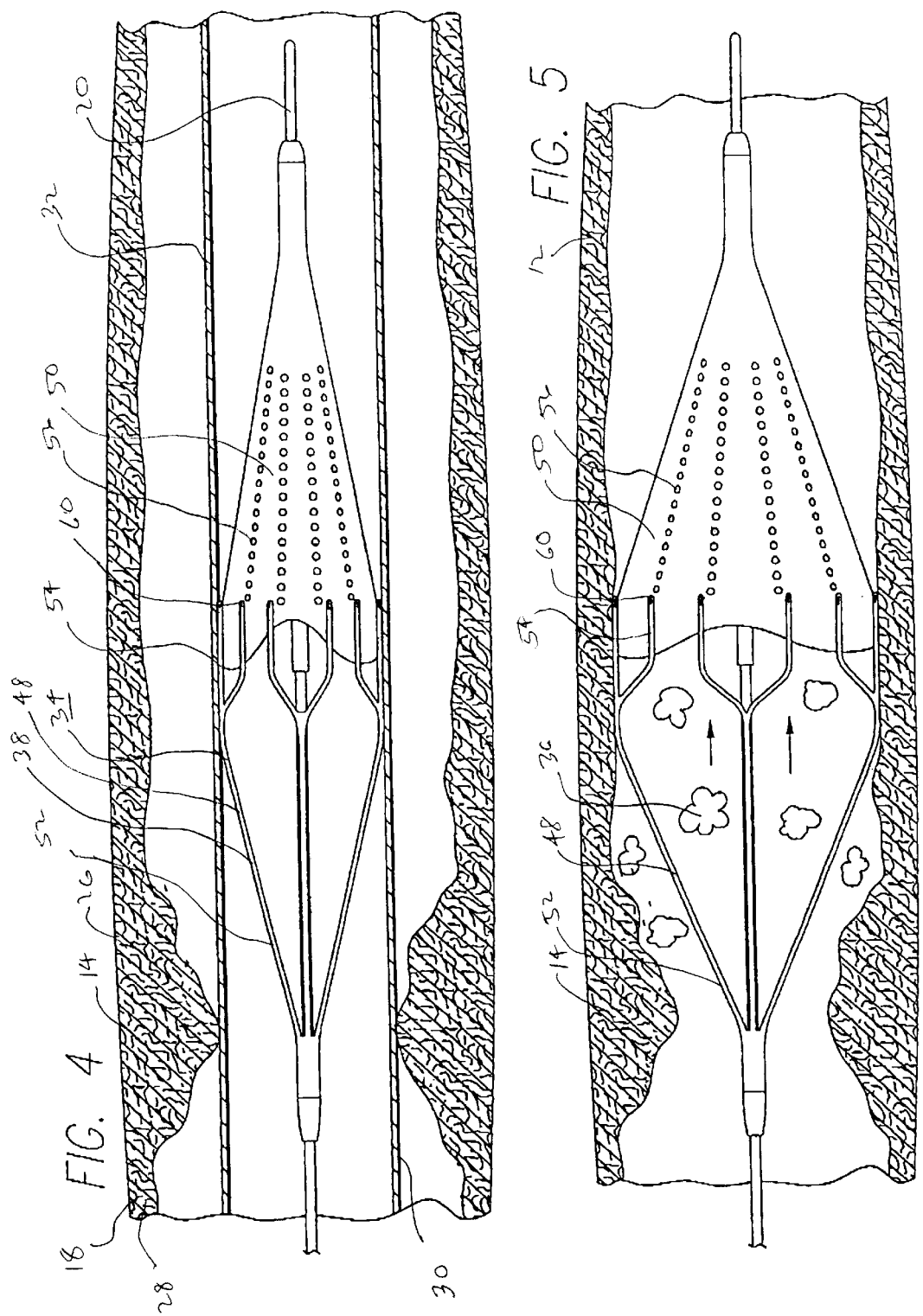

EXPANDABLE CAGE EMBOLIC MATERIAL FILTER SYSTEM AND METHOD

BACKGROUND OF THE INVENTION

The present invention relates generally to a system which can be used when an interventional procedure is being performed in a stenosed or occluded region of a blood vessel to enhance the expansion and deployment of an expandable cage filter for filtering the blood in a blood vessel so as to capture embolic material that may be created and released into the bloodstream during the procedure. The system of the present invention is particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of a filter or trap downstream from the treatment site to capture embolic debris before it reaches the smaller blood vessels downstream. However, there have been problems associated with filtering systems, particularly during the expansion and deployment of the filter within the blood vessel. The filter stiffness profile is important for enabling the filter to track through the very tight and small anatomy in the blood vessels. If the filter is substantially flexible and then becomes substantially stiff, it tends to generate kinks in the guide wire, making it difficult to track through the blood vessel. Further, the filtering system may not expand substantially freely and deploy distal to the interventional procedure site, inhibiting the filtering of embolic material.

What has been needed is a reliable system and method for treating stenosis in blood vessels which improves the expansion and deployment characteristics of an expandable cage filter to enable the expandable cage to be substantially-freely expandable in the blood vessel from unexpanded condition thereof, for capturing embolic debris in the bloodstream that can cause blockage in vessels at downstream locations. The system and method should be capable of filtering embolic debris which may be released into the bloodstream during the treatment to the vessel, and yet allow a sufficient amount of oxygenated blood to flow past the filtering device to supply vital organs downstream from the treatment site. The system and method should be relatively easy for a physician to use and should provide a nearly failsafe filtering system capable of removing embolic debris released into the bloodstream. Moreover, such a system should be relatively easy to deploy and remove from the patient's vasculature. The inventions disclosed herein satisfy these and other needs.

SUMMARY OF INVENTION

The present invention provides a system and method for capturing and retaining embolic debris from a blood vessel which may be created during the performance of a therapeutic interventional procedure, such as a balloon angioplasty or stenting procedure, in order to prevent the embolic debris from lodging and blocking blood vessels downstream from the interventional site. The present invention is particularly useful while performing an interventional procedure in vital arteries, such as the carotid arteries, in which critical downstream blood vessels can become blocked with embolic debris, including the main blood vessels leading to the brain or other vital organs. As a result, the present invention provides the physician with a higher degree of confidence that any and all embolic debris is being collected and removed from the blood vessel when performing high-risk interventional procedures.

The present invention is deployed in the blood vessel at a location distal to the area of treatment in the interventional procedure site, passes the blood therethrough to enable blood to flow past the filter, and filters the blood to capture and retain any embolic debris which may be created during the interventional procedure.

In the present invention, the system includes an emboli-capturing filter attached to an expandable cage to filter the blood vessel and to capture and retain embolic material, and a plurality of openings in the filter to enable some amount of blood to flow past the deployed filter. The emboli-capturing filter of the present invention directs the blood flow through the area where the interventional procedure is to be performed and through the filter located distal to the interventional site, which is designed to capture and retain friable plaque deposits. Additionally, the present invention allows blood to flow past the filter to provide a substantially continuous stream of blood to the organs located downstream.

In an embodiment of the present invention, the system includes an expandable cage and filter which can be deployed within the blood vessel for filtering blood flow past the expandable member at a location distal downstream to the interventional procedure site. The expandable cage and filter is adapted to be relatively flexible towards the distal end, and relatively stiff towards the proximal end, to provide gradual stiffness for efficient tracking through the blood vessel, and for effective expansion and deployment of the expandable cage and filter. The expandable cage and filter may include a plurality of struts, adapted to be expandable from unexpanded condition thereof. The expandable cage and filter may further include filter material which includes a plurality of openings which may be formed therein, which are adapted to pass blood therethrough while preventing embolic material from passing therethrough.

In a particular embodiment of the present invention, the system comprises a catheter, including an elongated shaft having a distal end portion adapted to be positioned in a blood vessel at an interventional procedure site. A filter device is adapted to be located in the distal end portion of the catheter shaft and is mounted on a guide wire, to be deployed distal to the interventional procedure site, and to pass blood therethrough to capture embolic material which may be released into the bloodstream during the interventional procedure. The filter device includes an expandable cage assembly, adapted to be expandable to capture embolic material, and to be collapsible to retain the captured embolic material. The expandable cage includes an element for varying the stiffness along the length of the expandable cage, for enabling the expandable cage to be substantially-freely expandable responsive thereto. The expandable cage is adapted to be positioned in the distal end portion of the guide wire, such that, for variable stiffness of the expandable cage, wherein the distal end portion is relatively flexible and the proximal end portion is relatively stiff, positioning of the expandable cage in the blood vessel is enhanced. The expandable cage further includes a plurality of struts for expansion thereof, and in another embodiment also includes a marker tip at a free end of each of the plurality of struts, adapted to be radiopaque, for enabling verification of the location of the expandable cage in the blood vessel and the opening or closing of the expandable cage.

Other features and advantages of the present invention will become more apparent from the following detailed description of the preferred embodiments of the invention, when taken in conjunction with the accompanying exemplary drawings.

BRIEF DESCRIPTION OF THE DRAWINGS

FIG. 1 is an elevational view, partially in section, depicting a first embodiment of the present invention disposed within the interval carotid artery of a patient, including a catheter, and an expandable cage and filter in unexpanded condition.

FIG. 2 is an elevational view, partially in section, similar to that shown in FIG. 1, wherein the expandable cage and filter is in expanded condition.

FIG. 4 is an elevational view, partially in section, depicting a second embodiment of the present invention disposed within the interval carotid artery of a patient, including a catheter, and an expandable cage and filter in unexpanded condition.

FIG. 5 is an elevational view, partially in section, similar to that shown in FIG. 4, wherein the expandable cage and filter is in expanded condition.

DETAILED DESCRIPTION OF THE PREFERRED EMBODIMENTS

Figure 3:
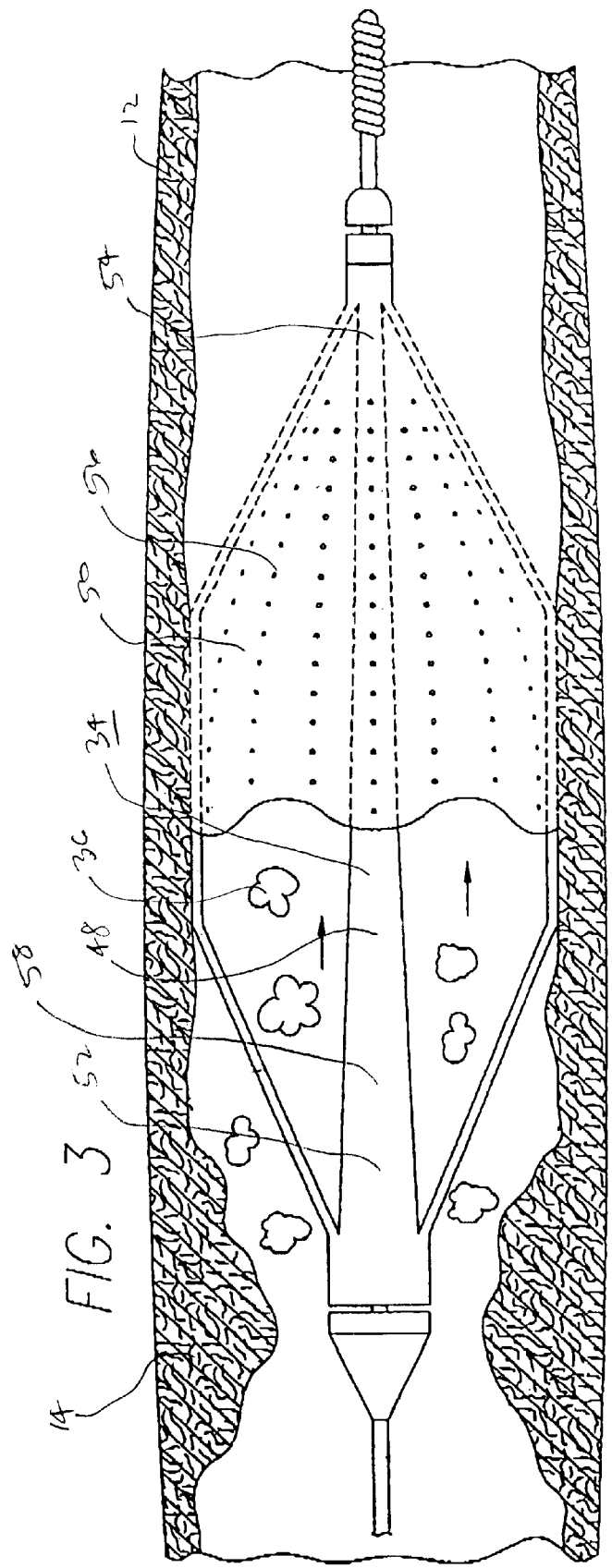
FIG. 3 is an elevational view, partially in section, of a version of the embodiment shown in FIG. 1, wherein the expandable cage is in expanded condition.

The present invention is directed to an improved system and method for efficiently and effectively enabling an interventional procedure to be performed in a blood vessel at an interventional procedure site. It is adapted to filter the blood in the blood vessel, so as to pass blood therethrough, and capture embolic material which may be released into the blood vessel during the interventional procedure. It is further adapted to enable an expandable cage and filter to be substantially-freely expandable in the blood vessel from unexpanded condition thereof, for enabling enhanced expansion and deployment of the expandable cage and filter. The embodiments of the improved system and method are illustrated and described herein by way of example only and not by way of limitation. While the present invention is described in detail as applied to the carotid arteries of the patient, and the disclosed interventional procedure is directed to a stenting procedure, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Referring now to the drawings, wherein like reference numerals denote like or corresponding parts throughout the drawing figures, and particularly to FIGS. 1–5, a system 10 is provided for enabling an interventional procedure to be performed in a blood vessel 12 at an area of treatment 14. The system 10 includes a catheter 16 adapted to enable the interventional procedure to be performed. As shown in FIGS. 1 and 4, the system 10 may be positioned in the catheter 16, and may be placed within the carotid artery 18 or other blood vessel of the patient, in the catheter 16, and the expandable cage and filter may guided into position by a guide wire 20. The guide wire 20 for example may be between one-hundred thirty and three hundred centimeters long. The guide wire 20 may include a coiled tip 22 at a distal end 24 of the guide wire 20. The carotid artery 18 may have the area of treatment 14, which may comprise the interventional procedure site, wherein atherosclerotic plaque 26 may have built up against the inside wall 28 which decreases the diameter of the carotid artery 18. As a result, blood flow may be diminished through this area. The catheter 16 may include an elongated shaft 30 having a distal end 32.

The therapeutic interventional procedure may comprise implanting an expandable interventional instrument at the interventional procedure site 14, to compress the build-up of plaque 26 of the stenosis against the inside wall 28, to increase the diameter of the occluded area 14 of the artery 18, and to help restore sufficient flow of blood to the downstream vessels leading to the brain. The expandable interventional instrument not only helps increase the diameter of the occluded area, but may help prevent restenosis in the area of treatment 14. The expandable interventional instrument may be adapted to be located in the distal end portion 32 of the catheter 16, and to be expanded and deployed at the interventional procedure site 14.

The system 10 includes a filter device 34 adapted to filter the blood in the blood vessel 12, so as to pass blood therethrough and capture embolic material 36 which may be released in the blood vessel 12 during the interventional procedure. The guide wire 20 and the catheter 16 are adapted to enable the filter device 34 to be placed within the carotid artery 18 or other blood vessel of the patient and guided into position distal to the area of treatment 14. The filter device 34 may include an expandable cage assembly 38 which is positionable proximate the distal end 24 of the guide wire 20, and which is adapted to be delivered to a position distal to the interventional procedure site 14 in unexpanded condition, by the guide wire 20 and in the catheter 16, and expanded and deployed distal to the interventional procedure site 14 upon retraction of the catheter 16. The expandable cage assembly 38 may be generally tubular-shaped. The expandable cage assembly 38 is adapted to be expandable to capture embolic material 36, and to be collapsible to retain the captured embolic material 36. The expandable cage assembly 38 may for example have a length of one-and-one-half to three-and-one-half centimeters.

The expandable case assembly 38 includes a distal end 40 and a proximal end 42. The diameter of the distal end 40 of the expandable cage assembly 38 is less than the diameter of the proximal end 42 of the expandable cage assembly 38, and the diameter of the expandable cage assembly 38 in unexpanded condition for example increases gradually along the length thereof from the distal end 40 to the proximal end 42. The distal end 24 of the guide wire 20 may extend for example two to four centimeters beyond the distal end 40 of the expandable cage assembly 38. A distal bushing 44 is mounted on the guide wire 20 at the distal end 40 of the expandable cage assembly 38, and a proximal bushing 46 is mounted on the guide wire 20 at the proximal end 42 of the expandable cage 38. The distal bushing 44 and the proximal bushing 46 are generally conical-shaped at the end portions thereof, for smooth transitions to the guide wire 20, and provide smooth interfacing surfaces for enabling the expandable cage assembly 38 to rotate, while preventing translational movement thereof.

The expandable cage assembly 38 may further include a plurality of struts 48, and filter material 50. Each of the plurality of struts 48 includes a proximal end 52 and a distal end 54. The filter material 50 is adapted to filter embolic material 36, so as to enable blood to flow therethrough and to prevent emboli 36 from passing therethrough, and may include a plurality of openings 56 therein. The filter material 50 may be comprised of filter material, and may extend for example relative to distal portions of the plurality of struts 48, either on the outside or the inside thereof. The filter material 50 may be generally parabolic-shaped. The expandable cage assembly 38 is adapted to support the filter material 50 for filtering the blood, while preventing gaps between the expandable cage assembly 38 and the vessel wall 28 of the blood vessel 12.

The expandable cage assembly 38 may further include an element 58 for enabling the plurality of struts 48 to be expandable in the blood vessel 12 distal to the interventional procedure site 14. The expansion enabling element 50 is adapted for example to enable the expandable cage assembly 38 to be relatively flexible at the distal end portion 40 thereof, and relatively stiff at the proximal end portion 42 thereof, for enabling the expandable cage assembly 38 to be expandable, and to be readily positionable in the blood vessel 12 distal to the interventional procedure site 14. The expansion enabling element 58 is adapted to control the expansion characteristics of the expandable cage assembly 38 along the entire length thereof. It may comprise for example variable dimensions of each of the plurality of struts 48 along the length thereof, to vary the stiffness along the length of each of the plurality of struts 48, for enabling expansion of the expandable cage assembly 38 responsive thereto. The thickness of each of the plurality of struts 48 may be substantially variable from the proximal end 52 to the distal end 54 thereof. The plurality of struts 48 may comprise a plurality of sets of opposed struts 48, and the expansion enabling element 58 may comprise variable inside and/or outside diameters between sets of opposed struts 48 along the length thereof, and the diameter of each of the opposed struts 48 may be either constant or variable.

The relative stiffness of the expandable cage assembly 38 is related to the ratio between the inside diameter and the outside diameter of the opposed struts 48, and/or the cross-section of each of the plurality of struts 48. In the embodiment of the invention shown in FIGS. 4–5, the plurality of struts 48 may each include at the distal end 54 thereof a marker tip 60, adapted to be radiopaque to enable observation thereof so as to enable verification of the opening or closing of the expandable cage assembly 38, and to be smooth, without rough edges, to prevent damage to the blood vessel wall 28 when the plurality of ribs 48 deploy.

In use, as illustrated in FIGS. 1–5, the system 10 may be positioned in the patient's vasculature utilizing any one of a number of different methods. In one preferred method of positioning, the catheter 16 may be placed in the blood vessel 12 by utilizing the guidewire 20 which is inserted into the patient's vasculature and manipulated by the physician to the area of treatment 14. Thereafter, once the guidewire 20 is in place, the catheter 16 may be maneuvered over the guidewire 20 (via a central lumen) using well-known over-the-wire techniques to place the catheter 16 at a location distal to the area of treatment 14. After the catheter 16 is in place, the catheter 16 may be retracted from enclosing the expandable cage assembly 38, to enable the expandable cage assembly 38 to expand and deploy distal to the area of treatment 14. The expansion and deployment of the expandable cage assembly 38 is enhanced by the expansion enabling element 58, whereby for example the thickness of each of the plurality of struts 48, which may be substantially variable from the thicker proximal end 52 to the thinner distal end 54 thereof, enables such enhanced expansion and deployment. Also, for example, the variable inside and/or outside diameters between sets of opposed struts 48 along the length thereof enables improved expansion and deployment of the expandable cage assembly 38.

Upon retraction of the catheter 16 to enable expansion and deployment of the expandable cage assembly 38, the expansion-enabling element 58 of the expandable cage assembly 38 provides for example relative stiffness proximate the proximal end 52 thereof, and relative flexibility proximate the distal end 54 thereof. This enables the expandable cage assembly 38 to expand, so as to enable the expandable cage assembly 38 to be expanded and deployed in the blood vessel 12 distal to the treatment area 14. In the embodiment shown in FIGS. 3–4, once the expandable cage assembly 38 is expanded, the marker tips 60 enable observation thereof for verification of expanding or collapsing of the expandable cage assembly 38. After the expandable cage assembly 38 is deployed in the treatment area 14, the catheter 16 may be extended to collapse and enclose the expandable cage assembly 38, so as to capture the embolic material 36 in the filter material 50, and the guide wire 20 and the catheter 16 with the collapsed expandable cage assembly 38 including the embolic material 36 therein may be withdrawn from the area of treatment 14.

The expandable cage assembly 38 may be comprised, for example, of a material having advantageous stiffness characteristics and being efficient to work with for forming thereof, such as a shape memory material as for example Nitinol, and may be formed, for example, by heat treating. The variable thickness for the expansion enabling element 58 of each of the plurality of struts 48 in the expandable cage assembly 38 may be formed for example by step drilling or milling. The distal bushing 44 and the proximal bushing 46 may be secured to the guide wire 20 for example by being glued by a medical grade adhesive, crimped, or welded by a laser thereto. The filter material 50, which may for example be comprised of polyurethane, may be secured to the plurality of struts 48 for example by gluing or heat treating. The marker tips 60 may be comprised of platinum or gold bands at the distal ends 54 of the plurality of struts 48.

It should be appreciated that the particular embodiments of the expandable cage assembly 38 are capable of being positioned in the blood vessel 14. However, other forms of the expandable cage assembly 38 may be utilized with the present invention without departing from the spirit and scope of the invention. For example, the expandable cage assembly 38 may further be comprised of other forms of material. Additionally, while the expandable cage assembly 38 is shown as in various shapes in the embodiments herein, it can be formed in any one of a number of different shapes depending upon the construction desired.

The catheter assembly 16 of the present invention may be formed of conventional materials of construction. The catheter shaft 30 can be made out of relatively inelastic materials such as polyethylene, polyvinyl chloride, polyesters and composite materials. The various components may be joined by suitable adhesives based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the effectiveness of performing interventional procedures by substantially retaining the unexpanded axial dimension of an expandable interventional instrument upon expansion thereof to accurately and effectively pin and compress plaque at the interventional procedure site. Further modifications and improvements may additionally be made to the system and method disclosed herein without the departing from the scope of the invention. Accordingly, it is not intended that the invention be limited, except as by the appended claims.

What is claimed:

1. A system for capturing embolic material which may be released into a blood vessel during a therapeutic interventional procedure, comprising:
   a catheter, including an elongated shaft, adapted to be positionable within the blood vessel and distal to an interventional procedure site, wherein the catheter shaft includes a distal end; and
   a filter device, adapted to be located in the distal end portion of the catheter shaft, to be deployed distal to the interventional procedure site, and to pass blood therethrough and to capture embolic material which may be released into the blood in the blood vessel during the interventional procedure, wherein the filter device includes an expandable cage assembly, adapted to be expandable to capture embolic material, and to be collapsible to retain the captured embolic material, wherein the expandable cage assembly includes a plurality of struts, adapted to be expanded from unexpanded condition thereof, and a filter material for filtering embolic material, extending about the plurality of struts, and means for varying the stiffness along the length of the expandable cage assembly for enabling the expandable cage assembly to expand freely responsive thereto, comprising variable dimensions of the plurality of struts along substantially the entire thereof.

2. The system of claim 1, wherein the expandable cage assembly is generally parabolic-shaped.

3. The system of claim 1, wherein the filter material is generally conical-shaped.

4. The system of claim 1, wherein the plurality of struts each include a variable thickness along the length thereof, and the variable dimensions comprise the variable thickness of each of the plurality of struts along the length thereof.

5. The system of claim 1, wherein the plurality of struts comprise a plurality of sets of opposed struts, and the variable dimensions comprise variable inside diameters between sets of opposed struts along the length thereof.

6. The system of claim 5, wherein each of the plurality of struts is uniform in thickness.

7. The system of claim 5, wherein each of the plurality of struts is variable in thickness.

8. The system of claim 1, wherein the plurality of struts comprise a plurality of sets of opposed struts, and the variable dimensions comprise variable outside diameters between sets of opposed struts along the length thereof.

9. The system of claim 8, wherein each of the plurality of struts is uniform in thickness.

10. The system of claim 8, wherein each of the plurality of struts is variable in thickness.

11. The system of claim 1, wherein the plurality of struts each includes a free end and a fixed end, further comprising the marker tip at a free end of each strut adapted to enable observation thereof so as to enable verification of the opening or closing of the expandable cage assembly.

12. The system of claim 1, wherein each of the plurality of struts includes a distal portion, and the filter material extends about the strut distal portion.

13. A system for capturing embolic material which may be released into a blood vessel during a therapeutic interventional procedure, comprising:

a catheter, including an elongated shaft, adapted to be positionable within the blood vessel and distal to an interventional procedure site, wherein the catheter shaft includes a distal end; and a filter device, adapted to be located in the distal end portion of the catheter shaft, to be deployed distal to the interventional procedure site, and to pass blood therethrough and to capture embolic material which may be released into the blood in the blood vessel during the interventional procedure, wherein the filter device includes an expandable cage assembly, adapted to be expandable to capture embolic material, and to be collapsible to retain the captured embolic material, wherein the expandable cage assembly includes a plurality of struts, adapted to be expanded from unexpanded condition thereof, and a filter material for filtering embolic material, extending about the plurality of struts, and means for varying the stiffness along the length of the expandable cage assembly for enabling the expandable cage assembly to expand responsive thereto, comprising variable dimensions of the plurality of struts along substantially the entire length thereof.

14. The system of claim 13, wherein the plurality of struts comprise a plurality of sets of opposed struts, and the variable means comprise variable dimensions which comprise variable inside diameters between sets of opposed struts along the length thereof.

15. The system of claim 13, wherein the plurality of struts comprise a plurality of sets of opposed struts, and the variable means comprise variable dimensions which comprise variable outside diameters between sets of opposed struts along the length thereof.

16. The system of claim 13, wherein the plurality of struts each includes a free end and a fixed end, further comprising the marker tip at a free end of each strut, adapted to be radiopaque to enable observation thereof so as to enable verification of the opening or closing of the expandable cage assembly.

17. A system for capturing embolic material which may be released into a blood vessel during a therapeutic interventional procedure, comprising:

a catheter, including an elongated shaft, adapted to be positionable within the blood vessel and distal to an interventional procedure site, wherein the catheter shaft includes a distal end; and means for filtering embolic material, adapted to be located in the distal end portion of the catheter shaft, to be deployed distal to the interventional procedure site, and to pass blood therethrough and to capture embolic material which may be released into the blood in the blood vessel during the interventional procedure, wherein the filtering means include an expandable cage assembly, adapted to be expandable to capture embolic material, and to be collapsible to retain the captured embolic material, wherein the expandable cage assembly includes a plurality of struts, adapted to be expanded from unexpanded condition thereof, and a filter material for filtering embolic material, extending about the plurality of struts, and means for varying the stiffness along the length of the expandable cage assembly for enabling the expandable cage assembly to expand freely responsive thereto, comprising variable dimensions of the plurality of struts along substantially the entire length thereof.

18. The system of claim 17, wherein the plurality of struts each include a variable thickness along the length thereof, and the variable dimensions comprise the variable thickness of each of the plurality of struts along the length thereof.

19. The method of claim 17, wherein expanding further comprises expanding the plurality of struts and the filter material extending thereabout responsive to the variable dimensions along the length thereof.

20. The method of claim 19, wherein the plurality of struts comprise a plurality of sets of opposed struts, and the variable dimensions comprise variable inside diameters between sets of opposed struts along the length thereof, and expanding further comprises expanding the plurality of sets of opposed struts responsive to the variable inside diameters therebetween along the length thereof.

21. A method of capturing embolic material which may be released into a blood vessel during a therapeutic interventional procedure, in a system which comprises catheter, including an elongated shaft, adapted to be positionable within the blood vessel and distal to an interventional procedure site, wherein the catheter shaft includes a distal end, and a filter device, adapted to be located in the distal end portion of the catheter shaft, to be deployed distal to the interventional procedure site, and to pass blood therethrough and to capture embolic material which may be released into the blood in the blood vessel during the interventional procedure, wherein the filter device includes an expandable cage assembly, adapted to be expandable to capture embolic material, and to be collapsible to retain the captured embolic material, wherein the expandable cage assembly includes a plurality of struts, adapted to be expanded from unexpanded condition thereof, and a filter material for filtering embolic material, extending about the plurality of struts, and means for varying the stiffness along the length of the expandable cage assembly for enabling the expandable cage assembly to expand responsive thereto, comprising variable dimensions of the plurality of struts along substantially the entire length thereof, wherein the method comprises:

positioning the catheter shaft in the interventional procedure site such that the expandable cage assembly is located within the blood vessel in the region at a location distal to the interventional procedure site;

expanding the expandable cage assembly within the blood vessel at the location distal to the interventional procedure site responsive to the stiffness varying means so as to capture embolic material;

performing the interventional procedure, which may release embolic material into the blood;

filtering the blood through the expandable cage assembly so as to capture embolic material which may be released into the blood upon performing the interventional procedure; and collapsing the expandable cage assembly so as to retain the captured embolic material.

* * * * *

UNITED STATES PATENT AND TRADEMARK OFFICE
CERTIFICATE OF CORRECTION

PATENT NO. : 6,575,995 B1
DATED : June 10, 2003
INVENTOR(S) : Benjamin Curtis Huter et al.

It is certified that error appears in the above-identified patent and that said Letters Patent is hereby corrected as shown below:

Column 9,
Line 25, change "a", to read -- the --.

Column 10,
Line 1, change "a", to read -- the --.

Signed and Sealed this

Seventh Day of October, 2003

JAMES E. ROGAN
*Director of the United States Patent and Trademark Office*